United States Patent [19]

Culbertson et al.

[11] Patent Number: 5,369,142
[45] Date of Patent: Nov. 29, 1994

[54] WATER SOLUBLE POLYMERS CONTAINING AMINO ACID RESIDUES FOR DENTAL RESTORATIVES

[75] Inventors: Billy M. Culbertson, Worthington; Elizabeth C. Kao, Westerville, both of Ohio

[73] Assignee: The Ohio State University, Columbus, Ohio

[21] Appl. No.: 3,971

[22] Filed: Jan. 15, 1993

[51] Int. Cl.$^5$ .......................... A61K 6/08; C08F 20/60
[52] U.S. Cl. ...................................... 523/116; 526/307; 526/312; 524/430; 524/494
[58] Field of Search ........................ 523/116; 522/149; 526/307, 312, 307.6; 524/430, 494

[56] References Cited

U.S. PATENT DOCUMENTS

| | | | |
|---|---|---|---|
| 3,655,605 | 4/1972 | Smith | 260/29.6 M |
| 4,016,124 | 4/1977 | Crisp et al. | 260/29.6 M |
| 4,089,830 | 5/1978 | Tezuka et al. | 260/29.6 H |
| 4,143,018 | 3/1979 | Crisp et al. | 260/29.6 M |
| 4,209,434 | 6/1980 | Wilson et al. | 260/29.6 H |
| 4,317,681 | 3/1982 | Beede et al. | 106/85 |
| 4,342,677 | 8/1982 | Muramatsu et al. | 523/116 |
| 4,360,605 | 11/1982 | Schmitt et al. | 523/116 |
| 4,374,936 | 2/1983 | Tomioka et al. | 523/116 |
| 4,376,835 | 3/1983 | Schmitt et al. | 523/116 |
| 4,663,409 | 5/1987 | Friends et al. | 526/242 |
| 5,063,257 | 11/1991 | Akahane et al. | 523/116 |
| 5,130,347 | 7/1992 | Mitra | 522/149 |

FOREIGN PATENT DOCUMENTS 57-16808 3/1982 Japan .

OTHER PUBLICATIONS

Barbucci et al, *Makromol. Chem.*, vol. 190 1989–pp. 2627–2638.
Varaprasad et al, *J. Polymer Sci, Polymer Chem. Ed.* vol. 22 1984, pp. 2131–2143.
Winston et al, Hydroxamic Acid Polymers Effect of Structure on the Selective Chelation of Iron in Water, 1978, pp. 597–603 vol. 11, No. 3.
Hoke and Robins, *J. Polymer Sci. Polymer Chem. Ed.* vol. 10, 1972, pp. 3311–3315, Preparation and Polymerization of 3–Acrylamido-3 Method Butaroic Acid.
Ritter and Rodewald, *Makromol Chem.* 1986, pp. 801–807 vol. 187.
Barbucci et al, *Macromolecules*, 1991, pp. 1249–1252 vol. 24.
Kulkarni et al, *J. Polymer Sci.*, 1961, pp. 491–503 vol. 54.
Winston, *Polymer News*, 1984, pp. 6–12 vol. 10, No. 1–"Bioactive Hydroxamic Acid Polymers for Iron Chelation".
Crisp et al, "Glass ionomer cement formulations. 11. The Synthesis of Novel Polycarboxylic Acids," 1980, pp. 1055–1063 vol. 59, No. 6.
Prosser et al, "Polyelectrolyte Cements", 1983 Developments in Ionic Polymer–1 Chap. 5.
Prosser et al, *J. Chem. Tech.*, 1979, pp. 69–87 "Lith-Ionomer Cements and Their Technoligical Applications".
Bowen et al, "Dental Composites/Glass Ionomers: The Materials" 1992, pp. 44–49 vol. 6.
Mitra, "Adhesion to Dentin and Physical Properties of a Light-Cured Glass Ionomer Liner/Base", 1991, pp. 72–74 vol. 70, No. 1.
Phillips et al, "Tensile bond strength between glass ionomer cements and composite resins" 1987, pp. 167–172 vol. 114.

(List continued on next page.)

*Primary Examiner*—Paul R. Michl
*Assistant Examiner*—LaVonda R. DeWitt
*Attorney, Agent, or Firm*—Frank H. Foster

[57] ABSTRACT

Glass ionomer cements for dental restoratives with improved physical properties are produced by the present invention. Acryloyl and methacryloyl derivatives of amino acids are used in the invention to copolymerize with acrylic acid, methacrylic acid or various acrylic acid-comonomer mixtures to produce water soluble polycarboxylic acids.

19 Claims, No Drawings

OTHER PUBLICATIONS

Hayakawa et al, "Adhesiveness of Amide Monomers to Tooth Substrate" pp. 165–171, 1991.

Wilson and Combe, "Effects of Glass Composition and Pretreatment on the Reactivity of Novel Glass Polyalkenoate Dental Cements" 1991 pp. 15–21.

Kaczmar and Traser, *Makromol. Chem.*, 1976, pp. 1981–1989.

Yoshida et al, "Light-scattering Study of Temperature Responsive Poly(Acryloyl-L-Proline Methyl Ester)" 1992, pp. 1141–1145 vol. 28, No. 9.

Prosser et al, "The Effect of Additives on the Setting Properties of a Glass–Ionomer Cement" 1982, pp. 1195–1198.

Wilson et al, "Glass Ionomer Cement" Quintessence Pub. Chicago, Ill. 1988.

Wilson et al., "Glass–Ionomer Cement Formulations II. The Synthesis of Novel Polycarboxylic Acids", *J. Dent Res*, vol. 59, No. 6, Jun. 1980, pp. 1055–1063.

WATER SOLUBLE POLYMERS CONTAINING AMINO ACID RESIDUES FOR DENTAL RESTORATIVES

TECHNICAL FIELD

The present invention relates to organic-inorganic hybrids, ionomer systems, useful for the preparation of dental and medical adhesives, bases, liners, luting agents, sealants, and filling materials for restorative and/or endodontic uses. The invention further relates to novel polymers for such dental and medical applications and their method of manufacture and compositions for setting and curing of dental and medical cement systems.

BACKGROUND ART

Human teeth often need repair due to destructive forces of injury, caries and aging. The restoration of teeth frequently requires the replacement of a core filling material.

Silicate cements have been used in the past for the repair of teeth and have the good properties of low thermal expansion, high abrasion resistance when not attacked by acids, and the ability to afford some caries protection by the liberation of fluoride ions.

Polycarboxylate cements are noted for their hydrophilic properties, good adhesion to tooth structure and apparent blandness. Polycarboxylate cements are based on zinc oxide or magnesium oxide or tin oxide and an aqueous solution of polyacrylic acid or an acrylic acid copolymer with other unsaturated carboxylic acids.

One of the most widely used filling materials is composite resins but these frequently possess coefficients of thermal expansion which are two to three times that of tooth material. This is a significant disadvantage and may result in increased microleakage and may lead to recurrent caries.

Glass ionomer cement filling materials have been previously developed which have addressed some of the above disadvantages of composite resin. Glass ionomer cement has strength characteristics similar to those cited above for silicate cements but is more resistant to acid attack. It is also bland, like the polycarboxylate cements, but with the added advantage of translucency.

The setting or hardening reaction of glass ionomer compositions occurs when a water soluble polymer having pendent carboxylic acid groups reacts with an ion-leaching glass powder. In the setting reaction, the glass powder behaves like a base and reacts with the acidic polyelectrolyte, i.e., ionomer, to form a metal polysalt (ionic cluster) which acts as the binding matrix. Water serves as a reaction medium, facilitating ion transport in what is essentially an ionic reaction. The setting reaction is characterized to be a chemically cured system that proceeds automatically upon mixing the ionomer and glass powder in the presence of water. The mixtures set or react to form a gel-like material within a few minutes and this material further hardens rapidly to develop the desired strength. Tartaric acid and other chelating agents are useful for modifying the rate of setting to thereby provide expanded working times for the composites or cements.

The ability of glass ionomer cements or composites to leach fluoride ions and to bond to tooth structure are their main advantages, since these materials are dynamic in nature, capable of ion-exchange at the tooth surface. Their anti-cariogenic properties, combined with molecular attachment to structure, make them the material of choice for treating early carious lesions or patients with a high caries incidence. However, glass ionomer materials are inherently brittle and can be prone to porosity, a further cause of weakness. As a result, the use of traditional glass ionomers has been limited to anteriors, non-stress bearing areas in gingival erosion, abrasive cavities and fissures. Glass ionomer cement materials continue to have significant limitations for use in permanent posterior, particularly with regard to large restorations.

A major problem with commercially used polymers for glass ionomers, such as poly(acrylic acid) (I) or poly(acrylic acid-co-itaconic acid) (II), resides in the direct or very close attachment of all the acid ($CO_2H$) groups to the polymer backbone as shown below.

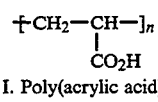

I. Poly(acrylic acid)

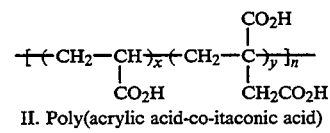

II. Poly(acrylic acid-co-itaconic acid)

U.S. Pat. No. 4,663,409 teaches the use of amino acid based monomers for improving the properties of contact lenses.

Therefore, it would be desirable to produce glass ionomer cement materials with significantly enhanced physical properties, with retention of all the positive features of these dental materials.

BRIEF DISCLOSURE OF INVENTION

Therefore, it is one object of the present invention to provide a dental filling material comprising a glass ionomer cement comprising an organic binder with amino acid functionalized, water soluble polycarboxylic acids.

Another object of the present invention is to provide amino acid functionalized glass ionomer dental cements with improved physical properties relative to glass ionomer cements comprising an organic binder with no amino acid functionalities. These improved physical properties include but are not limited to enhanced use in occlusal surfaces of permanent posterior teeth, enhanced adhesion to tooth structure, increased tensile and compressive strength, and improved fracture and wear resistance.

The present invention relates to glass ionomer polymers that have pendent amino acid residues, specifically, acrylic acid polymers or copolymers of acrylic acid and, for example itaconic acid, which are modified to contain acryloyl or methacryloyl derivatives of amino acids. These materials provide water soluble polymers with pendent amino acid residues. In contrast to conventional, non-amino acid derivatized acrylic acid polymers and/or acrylic acid-itaconic acid copolymers, the polymers of the present invention produced by incorporation of the amino acid based monomers have some of the carboxylic acid residues removed at various spacer distances from the backbone of the parent polymer, with the spacer distance determined by the type of amino acid monomer used for the polymer synthesis. Polymers of this type also have pendent acid groups with a wider range of pKa values, reduced steric hinderance of some of the carboxylic acid groups, and an enhanced concentration of primary carboxylic acid residues, in contrast to current conventional glass ionomer copolymer materials derived from acrylic acid and itaconic acid. Amino acid containing polymers of the type described in the present invention have greater degrees of freedom to react with $Ca^{2+}$ and $Al^{3+}$ ions in reactive glass powders and the $Ca^{2+}$ or $Al^{3+}$ cations by the present invention can more readily form ionic clusters in the vitrified matrix making up the cured glass ionomer composite than would be possible using conventional non-amino acid ionomer cements. The polymers of the present invention having carboxylic acid groups residing at various distances from the polymer backbone, exhibit greater conformational flexibility and more homogeneity in carboxylate anion-metal cation cluster formation.

Thus, in one embodiment the present invention relates to a water soluble polymer composition comprising the reaction product of A and B, wherein A is selected from the group consisting of polyalkenoic mono-, di-, and tricarboxylic acids and homopolymers and copolymers thereof, and wherein B is selected from the group of synthetic and natural amino acids, whereby the polyalkenoic acid is derivatized with pendent amino acid residues, and wherein the reaction product of A and B is then homopolymerized or copolymerized with one or more other monomers to form a water soluble polymer.

DETAILED DESCRIPTION

The term "ionomer" herein refers to a polymer having sufficient pendent ionic groups to undergo a setting reaction, also called "cure" herein, in the presence of a reactive powder and water.

By "reactive powder" herein is meant a powdered or otherwise surface active metal oxide or hydroxide, mineral silicate, or ion leachable glass that is capable of reacting with the ionomer in the presence of water to form a hydrogel. Examples of such reactive powders include, not by way of limitation, calcium-containing and aluminum-containing materials such as calcium alumino silicate glass, calcium alumino fluorosilicate glass, calcium aluminum fluoroborosilicate glass, and like materials known in the art of glass ionomer cements.

By "glass ionomer cement" herein is meant the unmixed or mixed but unset and uncured combination of an ionomer, reactive powder, and other optional ingredients, such as water. Such cement systems include kits in which the ionomer is employed as a concentrated aqueous solution, for mixing directly with the reactive powder as well as kits in which the ionomer is employed as a dry blend with the powder, for later mixing with water. The cements of the present invention may be further modified to include visible light-curable formulations.

The term "working time" as used herein, refers to the time between the beginning of the setting reaction, i.e., when the ionomer and reactive powder are combined in the presence of water, and the time the setting reaction proceeded to the point at which it is no longer practical to perform further physical work upon the system, e.g. spatulate it or reshape it, for its intended dental or medical application.

By "setting time" herein is meant the time between the beginning of the setting reaction in a restoration, and the time sufficient hardening has occurred to allow subsequent clinical procedures to be performed on the surface of the restoration.

Ionomers of the present invention comprise polymers having one or more different amino acid residues pendent on the backbone of the polymers, along with varying amounts of carboxylic acid residues derived from monomers of acrylic acid, maleic acid, fumaric acid, tartaric acid, itaconic acid, crotonic acid, methacrylic acid, etc., the acid chlorides thereof and the acid anhydrides thereof, chloro or bromo derivatives thereof, and mixtures and copolymers thereof. For such polymers, the pendent ionic groups must be sufficient in number or percent by weight to bring about the setting or cure reaction in the presence of the reactive powder.

The standard type of polyalkenoic acids used for preparing ionomers useful for glass ionomer cement systems include those homopolymers and copolymers of unsaturated mono, di- or tricarboxylic acids commonly used to prepare water soluble carboxylic acid containing polymers. Representative polyalkenoic acids are described, for example, in U.S. Pat. Nos. 3,655,605; 4,016,124; 4,089,830; 4,143,018; 4,342,677; 4,360,605; 4,376,835; and 5,130,347. The particularly preferred monomers to produce the standard polyalkenoic acids are acrylic acid, itaconic acid and maleic acid, and the chlorides or anhydrides thereof.

The synthetic and natural amino acids that can be used according to the present invention to modify the binder of a glass ionomer dental cement by forming the acryloyl or methacryloyl functionalized monomers for this invention include, but are not limited to, glycine, glycylglycine, alanine, valine, leucine, isoleucine, phenylalanine, tyrosine, proline, hydroxyproline, serine, threonine, 3-amino-3-methylbutanoic acid, 6-aminocaproic acid, aminobenzoic acid (meta and para), 4-aminosalicylic acid, iminodiacetic acid, lanthionine, methionine, aspartic acid, glutamic acid, lysine, delta-aminolevulinic acid, beta-alanine, alpha-aminobutyric acid, gamma-aminobutyric acid, gamma, epsilon-diaminopimelic acid, gamma, alpha-diaminobutyric acid, ornithine, omega-aminododecanoic acid, beta-cyanoalanine, epsilon-methylhistidine, canavanine, djenkoic acid, 1-azaserine, gamma-methylene glutamic acid, N-methyl tyrosine, arginine, tryptophan, norvaline, cystine, cysteine, and hydroxylysine.

The invention is not limited to only the acryloyl or the methacryloyl derivatives of the glycylglycine peptide unit. The many other polypeptide fragments known to those skilled in the art may also be treated according to the present invention with acryloyl or methacryloyl acid chloride or anhydride to produce new monomers suitable for the polymers in the dental cements of the present invention. For example, the dimer of glutamic acid, glycine-glutamic acid peptide unit, etc., reaction with acryloyl chloride would produce a monomer having high acid and amide group content and thereby be useful herein.

The acryloyl or methacryloyl derivatives of amino acids are prepared by known synthetic techniques, described in the public literature, and referred to as the Schotten-Baumann reaction. For example and not by way of limitation, aqueous solutions of the sodium salt of the respective amino acid, cooled at 0°–5° C., was reacted with acryloyl or methacryloyl, where the acid chloride was added cautiously with vigorous stirring and the system maintained under a nitrogen sparge. After completion of addition and a short reaction time, ca. 1 hour, the solution was carefully acidified to a pH of about 1.5 to 3.0, using 6N HCl. In the case where the monomer was extremely water soluble, a salt (NaCl) was added to help "salt out" the product. The mixture may be extracted with solvents such as chloroform or ethyl acetate, and the combined extracts dried over magnesium sulfate. Evaporation of the solvent, recovery of the monomer and recrystallization of the monomer from suitable solvents produced the pure monomer for polymerization.

Methods to prepare the copolymers, via free-radical polymerization, are well described in the polymer literature. (See, for example, Crisp et al., "Glass ionomer cement formulations. II. The synthesis of novel polycarboxylic acids.", *J. Dent. Res.*, 59(6):1055–1063, (1980)).

By the present invention were prepared N-acryloyl-glutamic acid (III) and N-acryloyl-epsilon-aminocaproic acid (IV) monomers.

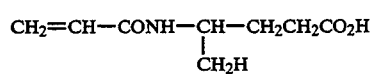

III.

IV.

Using standard free radical polymerization techniques, monomers III. and IV. were used according to the present invention to prepare water soluble, acrylic acid copolymers V. and VI. with pendent amino acid residues.

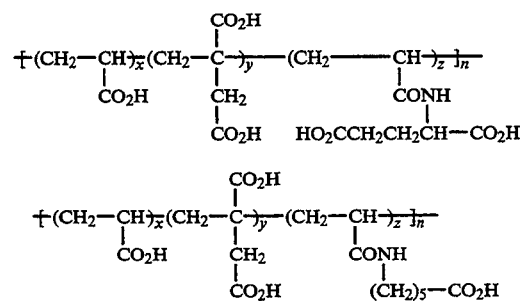

Copolymers V. and VI. have three different monomer residues, in contrast to I and II, and possess the following features:

a) a mixture of primary, secondary, and tertiary carboxylic acid groups.
b) greater degrees of steric freedom for the carboxylic acid groups to react with the reactive powder, such as calcium aluminosilicate glass and for ion cluster formation.
c) the acid groups have a wider pH range than the pH range of conventional glass ionomer polycarboxylic acid binders.
d) amide groups which offer additional promotion of adhesion to tooth structure.
e) retention of good biocompatibility, especially when natural amino acids are used.

By the present invention, novel polymer compositions are prepared, and the compositions are useful in preparing improved dental restorative materials comprising glass ionomer cements. Examples 20 and 21, below, clearly show that the materials of the present invention containing amino acid residues gave improved mechanical properties when compared to the Fuji II control system of Example 19.

In another embodiment, the present invention is directed to a method of repairing primary or permanent teeth or dental implants comprising:

a) applying to a surface of a primary or a permanent tooth or dental implant, in an amount and of configuration sufficient to effect the desired repair, a curable dental filling material comprising (1) a water soluble polymer composition comprising the reaction product of A and B, wherein A is selected from the group consisting of polyalkenoic mono-, di-, and tricarboxylic acids and homopolymers and copolymers thereof, and wherein B is selected from the group of synthetic and natural amino acids, whereby the polyalkenoic acid is derivatized with pendent amino acid residues, and wherein the reaction product of A and B is then homopolymerized or copolymerized with one or more other monomers to form a water soluble polymer; and (2) a reactive powder; and b) allowing the curable dental filling material to cure or set in the desired configuration.

The invention will be further understood by reference to the following examples which are not intended to represent any limitation of the scope of the invention.

EXAMPLE 1

Synthesis of N-Acryloylglutamic Acid

A reaction flask was charged with 120 ml distilled water, 48.0 g (1.2 mol) of sodium hydroxide and 58.8 g (0.4 mol) of glutamic acid. After cooling to 0° C., acryloyl chloride, 36 g (0.4 mol) was added over 1 hour to the stirred solution. After stirring for an additional 1 hour, the solution was acidified to pH of 2 with the addition of a concentrated HCl-H$_2$O (1:1) solution. After saturation of the solution with sodium chloride, ethyl acetate was used to extract the product. After drying the combined extracts over anhydrous magnesium sulfate, the ethyl acetate was evaporated to recover the crude product in greater than 60% yield. After recrystallization from ethyl acetate the white, crystalline N-acryloylglutamic acid had a melting point of 125°–127° C.

EXAMPLE 2

Synthesis of N-Acryloyl-6-aminocaproic Acid

Using the same procedure as previously described except substituting 6-aminocaproic acid for the glutamic acid, the crude product was obtained in greater than 85% yield. After crystallization from water or ethyl acetate, the white, crystalline N-acryloyl-6-aminocaproic acid had a melting point of 88°–90° C.

EXAMPLE 3

Synthesis of N-Methacryloylglutamic Acid

Using the same procedure as described in Example 1 except substituting methacryloyl chloride for acryloyl chloride, the white, crystalline monomer was obtained in high yield (greater than 80%) with a melting point of 131.5°–133.5° C.

EXAMPLE 4

Synthesis of N-Methacryloyl-6-aminocaproic Acid

Using the same procedure as Example 2 except for substituting the appropriate starting materials, the white crystalline monomer was obtained in high yield (greater than 85%) with a melting point of 52°–54° C.

EXAMPLE 5

Synthesis of N-Acryloylglycine

Using the same procedure of Example 1 except for substituting the appropriate starting materials, the white crystalline monomer was obtained in good yield, having a melting point of 134°–135° C.

EXAMPLE 6

Synthesis of N-Methacryloylglycine

Using the procedure of Example 1 except for substituting the appropriate starting materials, the white crystalline monomer was obtained in good yield, having melting point of 103°–105° C.

EXAMPLE 7

Synthesis of N-Methacryloylglycylglycine

Using Example 1, glycylglycine was reacted with methacryloyl chloride in water at −10° C. After adjustment to a pH of 3, the white slurry was washed with ethanol to remove sodium chloride and water. The product was dried at 80° C. to obtain a good yield (>75%) product with a melting point of 200°–201° C.

EXAMPLE 8

Synthesis of 3-Acrylamido-3-methylbutanoic

Using the procedure of Hoke and Robins (*J. Polymer Sci., Polymer Chem. Ed.*, 120, 3311–3315, 1972), 3-methylcrotonic acid was treated with acrylonitrile in a water-acid (sulfuric acid) solution containing hydroquinine inhibitor. The solution was heated at 45° C. for 8 hours after which the solution was cooled and extracted with chloroform. The chloroform extracts were dried over anhydrous magnesium sulfate and the solvent removed to obtain a good yield (>75%) of crude product. After recrystallization from a mixture of methyl ethyl ketone/petroleum ether, the monomer had a melting point of 93°–95° C.

EXAMPLE 9

Synthesis of N-Acryloyl-p-aminobenzoic Acid

The monomer was prepared from p-aminobenzoic acid reaction with acryloyl chloride, per Example 1. The monomer was recrystallized from an ethanol-water mixture and dried to produce a crystalline solid with a melting point of 249°–253° C.

EXAMPLE 10

Synthesis of N-Acryloyl-beta-alanine

This amide monomer was prepared from acryloyl chloride and beta-alanine per Example 1 procedure, with the recrystallized (ethyl acetate solvent) product having a melting point of 97°–99° C.

EXAMPLE 11

Synthesis of Poly(acrylic Acid-co-itaconic Acid co-N-acryloylglycine)

The procedure used for the copolymer production was described by Wilson et al *J. Dent. Res.* 59(6):1055–1063, June 1980. According to the procedure, the reactants are divided into three parts. Solution I contained ammonium persulfate dissolved in deionized water. Solution II contained the total monomers feed dissolved in a deionized water-isopropanol mixture. Solution III contained ammonium persulfate in deionized water. Solution I was contained in a reactor equipped with a thermometer, stirrer and nitrogen sparge tube. After a nitrogen sparge to rid the solution of dissolved oxygen, the temperature in the reaction was raised to 80°–100° C., while maintaining nitrogen purging. Solutions II and III were added progressively to the reaction flask over a period of 2 hours with continuous stirring. When the addition was complete, the contents of the reactor were maintained at the controlled temperature for a further 2 hours, with continuous stirring and purging. Finally, the solution was concentrated by vacuum distillation and the product recovered by freeze-drying. The powder obtained by freeze-drying was dissolved in methyl alcohol and filtered. With stirring, the methanol solution was combined slowly with diethyl ether to recover the polymer. After drying, the copolymer with X:Y:Z monomer molar feed ratio (10:1:1) was suitable for evaluation in a glass ionomer formulation. The GPC estimated molecular weight and dispersivity were, respectively, $Mw=60,000$ g/mole and 3.55. Spectroscopic (NMR and FT-IR) were supportive of the copolymer having the three residues.

EXAMPLE 12

Synthesis of Poly(acrylic Acid-co-itaconic Acid-co-N-acryloyl-6-aminocaproic Acid)

Using Example 11 procedure, the copolymer with monomer molar feed ratios X:Y:Z: (6:1:1) produced had GPC estimated molecular weight and dispersivity of 139,000 g/mole and 5.87. The presence of aminocaproic acid residues in the copolymers tended to increase the viscosity of aqueous solutions, compared to acrylic acid-itaconic acid copolymers. Spectroscopic (NMR and FT-IR) were supportive of the polymer structure, i.e., the copolymer having the three monomer residues.

EXAMPLE 13

Synthesis of Poly(acrylic Acid-co-itaconic Acid-co-N-acryloyl-p-aminobenzoic Acid)

Using the procedure of Example 11, the copolymer with monomer feed ratios X:Y:Z: (6:1:1) that was produced had GPC estimated $Mw=17,000$ g/mole and dispersivity of 2.40. The FT-IR and NMR spectra were supportive of the presence of all three monomer residues.

EXAMPLE 14

Synthesis of Poly(acrylic acid-co-itaconic acid-co-N-acryloylglutamic acid)

Using Example 11 procedure, the copolymer monomers feed ratio X:Y:Z: (10:1:1) produced had a GPC estimated $Mw=108,000$ g/mole and dispersivity=2.59. The copolymer was readily soluble in water.

EXAMPLE 15

Synthesis of Poly(acrylic Acid-co-N-acryloylglutamic Acid)

Using Example 11 procedure, the copolymer monomer feed ratio of X:Y (2:1) produced a polymer having a GPC estimated of $Mw=242,000$ g/mole and dispersivity of 5.74. The copolymer was readily soluble in water.

EXAMPLE 16

Synthesis of Poly(acrylic acid-co-N-acryloylglutamic acid)

Using the procedure of Example 11, the copolymer monomer feed ratio of X:Y (4:1) produced a polymer having GPC estimated molecular weight of 122,000 g/mole and dispersivity of 3.86. The copolymer was readily soluble in water.

EXAMPLE 17

Synthesis of Poly(acrylic Acid-co-N-acryloylglutamic Acid)

Using the procedure of Example 11, the copolymer monomer feed ratio of X:Y (6:1) produced a polymer having GPC estimated molecular weight and dispersivity, respectively, of 140,000 g/mole and 3.58. The copolymer was readily soluble in water.

EXAMPLE 18

Synthesis of Poly(acrylic Acid-co-N-acryloylglycine-co-N-acryloylglutamic Acid)

The three monomers were combined and polymerized per Example 11 method, giving a copolymer having X:Y:Z feed ratios of 6:1:1 and GPC estimated Mw=55,000 g/mole and dispersivity of 2.85. The FT-IR and NMR spectra were supportive of the polymer having all three monomer residues. The copolymer was readily soluble in water.

The procedures used to prepare samples for mechanical properties testing were as follows:

1. The freeze dried copolymers were dissolved in deionized water at a 50:50 (W:W) ratio.
2. The viscous solutions were combined (mixed well) with the reactive glass powder in a glass/liquid (2.75/1, wt/wt) ratio. The reactive glass was a calcium fluoroaluminosilicate powder supplied by GC America, with the powder containing tartaric acid and used in the Fuji II glass ionomer system.
3. The working and setting time of both the inventive and Fuji II control were evaluated.
4. The inventive and Fuji II control were fabricated into cylindrical specimens (6mm diameter by 12 mm length) for the compressive and diametral tensile strength testing and into 25 mm long 3 mm wide×3 mm high specimens for the flexural strength testing.
5. After setting (hardening) achieved, all samples were aged 24 hours in water at 37° C. prior to testing.
6. All testing achieved per NISI-ADA 1990 specifications for glass ionomer cements.

EXAMPLE 19

Glass Ionomer Control Properties

The Fuji II glass ionomer control (model system) was prepared per manufacturing directions, with formulation showing a working time of 2.5 minutes and a setting time of 4.5 minutes. The compressive and diametral tensile strength and flexural strength were, respectively, 168, 13.5 and 23.3 MPa.

EXAMPLE 20

Inventive Glass Ionomer Based on N-Acryloylglutamic Acid Copolymer

The aqueous solution of the copolymer of Example 11 was blended with the Fuji II glass powder at a powder:liquid ratio of 2.7:1 giving a working time of 2 minutes and setting time of 4 minutes. The compressive and diametral tensile strength and flexural strength were, respectively, 195, 22, and 48.5 MPa.

EXAMPLE 21

Inventive Glass Ionomer Based on N-Acryloyl-6-aminocaproic Acid Copolymer

The aqueous solution of the copolymer of Example 12 was blended with the Fuji II glass powder at a powder:liquid ratio of 2.7:1 giving a working time of 3.0 minutes and a setting time of 6.0 minutes. The compressive and diametral tensile strength and flexural strength were, respectively 173, 18.2, and 37.3 MPa.

TABLE 1

| System | Inventive Glass Ionomer Cements vs. Fuji II | | |
|---|---|---|---|
| | Compression | Diametral Tensile | Flexural |
| Fuji II | 168 (24,360) | 13.5 (1958) | 23.3 (3379) |
| Ex. 20 | 195 (28,275) | 22.0 (3190) | 48.5 (3379) |
| Ex. 21 | 173 (25,085) | 18.2 (2639) | 37.3 (5408) |

Units are given in MPa and (psi). Examples 20 and 21 clearly show that the materials of the present invention containing amino acid residues gave improved mechanical properties when compared to the Fuji II control system of Example 19.

The materials of the present invention are useful as glass ionomer cements, in the preparation of dental and medical adhesives, sealants, liners, luting agents, and filling materials for restorative and endodontic uses.

While certain preferred embodiments of the present invention have been disclosed in detail, it is to be understood that various modifications may be adopted without departing from the spirit of the invention or scope of the following claims.

We claim:

1. A curable water soluble polymer composition comprising the reaction product of A and B, wherein A is selected from the group consisting of polyalkenoic mono-, di-, and tricarboxylic acids and homopolymers and copolymers thereof, and wherein B is selected from the group of synthetic and natural amino acids, whereby the polyalkenoic acid is derivatized with pendent amino residues, and wherein the reaction product of A and B is then homopolymerized or copolymerized with one or more other monomers to form a curable water soluble polymer, the composition further comprising C, wherein C is a different amino acid than B.

2. The composition of claim 1 wherein A is selected from the group consisting of monomers of acrylic acid, maelic acid, fumaric acid, tartaric acid, itaconic acid, crotonic acid, methacrylic acid, methacryloyl chloride, acryloyl chloride, the acid chlorides thereof, the acid anhydrides thereof, chloro or bromo derivatives thereof, and mixtures thereof.

3. The composition of claim 1 wherein B is selected from the group consisting of glycine, glycylglycine, alanine, valine, leucine, isoleucine, phenylalanine, tyrosine, proline, hydroxyproline, serine, threonine, 3-amino-3-methylbutanoic acid, 6-aminocaproic acid, aminobenzoic acid (meta and para), 4-aminosalicylic acid, iminodiacetic acid, lanthionine, methionine, aspartic acid, glutamic acid, lysine, delta-aminolevulinic acid, beta-alanine, alpha-aminobutyric acid, gamma-aminobutyric acid, gamma, epsilon-diaminopimelic acid, gamma, alpha-diaminobutyric acid, ornithine, omega-aminododecanoic acid, beta-cyanoalanine, epsilon-methylhistidine, canavanine, djenkoic acid, 1-azaserine, gamma-methylene glutamic acid, N-methyl tyrosine, arginine, tryptophan, norvaline, cystine, cysteine, and hydroxylysine.

4. The composition of claim 1 wherein A is selected from the group consisting of acrylic acid, itaconic acid, and maleic acid, and B is glycine.

5. The composition of claim 1 wherein A is selected from the group consisting of acrylic acid, itaconic acid, and maleic acid, and B is glycylglycine.

6. The composition of claim 1 wherein A is selected from the group consisting of acrylic acid, itaconic acid, and maleic acid, and B is glutamic acid.

7. The composition of claim 1 wherein A is a copolymer of acrylic acid and itaconic acid and B is glycylglycine.

8. A mixture comprising:
   a) a water soluble polymer composition comprising the reaction product of A and B, wherein A is selected from the group consisting of polyalkenoic mono-, di-, and tricarboxylic acids and homopolymers and copolymers thereof, and wherein B is selected from the group of synthetic and natural amino acids, whereby the polyalkenoic acid is derivatized with pendent amino acid residues, and wherein the reaction product of A and B is then homopolymerized or copolymerized with one or more other monomers to form a water soluble polymer; and
   b) a reactive powder.

9. The mixture of claim 8 wherein the reactive powder is selected from the group consisting of powdered or otherwise surface active metal oxides or hydroxides, mineral silicates, and ion leachable glass that is capable of reacting with the water soluble polymer composition in the presence of water.

10. The mixture of claim 8 wherein the reactive powder is selected from the group consisting of calcium alumino silicate glass, calcium alumino fluorosilicate glass, calcium aluminum fluoroborosilicate glass, and the like.

11. The mixture of claim 8 further comprising water.

12. The mixture of claim 11 which after setting has compression strengths exceeding 170 MPa, diametral strengths exceeding 18 MPa, and flexural strengths exceeding 37 MPa.

13. A dental filling composition comprising the mixture of claim 8.

14. A dental filling material comprising the mixture of claim 11.

15. The dental filling material of claim 13 comprising a glass ionomer dental cement.

16. A glass ionomer dental cement comprising the mixture of claim 8.

17. A dental filling material comprising an acrylic acid-containing curable water soluble copolymer comprising moieties of acrylic acid and at least one other unsaturated carboxylic acid, and said copolymer further comprising at least one moiety derived from an amino acid-containing monomer.

18. The dental filling material of claim 17 further comprising a reactive powder selected from the group consisting of calcium alumino silicate glass, calcium alumino fluorosilicate glass, calcium aluminum fluoroborosilicate glass, and the like.

19. A method of repairing primary or permanent teeth or dental implants comprising:
   a) applying to a surface of a primary or a permanent tooth or dental implant, in an amount and of configuration sufficient to effect the desired repair, a curable dental filling material comprising (1) a water soluble polymer composition comprising the reaction product of A and B, wherein A is selected from the group consisting of polyalkenoic mono-, di-, and tricarboxylic acids and homopolymers and copolymers thereof, and wherein B is selected from the group of synthetic and natural amino acids, whereby the polyalkenoic acid is derivatized with pendent amino acid residues, and wherein the reaction product of A and B is then homopolymerized or copolymerized with one or more other monomers to form a water soluble polymer; and (2) a reactive powder; and
   b) allowing the curable dental filling material to cure or set in the desired configuration.

* * * * *